United States Patent
Malamud

(10) Patent No.: US 6,483,890 B1
(45) Date of Patent: Nov. 19, 2002

(54) DIGITAL X-RAY IMAGING APPARATUS WITH A MULTIPLE POSITION IRRADIATION SOURCE AND IMPROVED SPATIAL RESOLUTION

(75) Inventor: Gabriel Malamud, Binyamina (IL)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 09/729,143

(22) Filed: Dec. 1, 2000

(51) Int. Cl.[7] .............................................. H05G 1/60
(52) U.S. Cl. ........................ 378/22; 378/10; 378/98.12; 378/137
(58) Field of Search ........................ 378/10, 22, 98.12, 378/137

(56) References Cited

U.S. PATENT DOCUMENTS

| | | | | |
|---|---|---|---|---|
| 4,384,359 A | | 5/1983 | Franke ........................... 378/9 |
| 4,637,040 A | | 1/1987 | Sohval et al. ................... 378/9 |
| 4,730,350 A | * | 3/1988 | Albert ........................... 378/10 |
| 4,926,452 A | * | 5/1990 | Baker et al. ..................... 378/22 |
| 5,020,086 A | * | 5/1991 | Peugeot ....................... 378/113 |
| 5,305,363 A | * | 4/1994 | Burke et al. ..................... 378/4 |
| 5,594,770 A | * | 1/1997 | Bowles et al. ................. 378/58 |
| 5,668,844 A | * | 9/1997 | Webber ........................... 378/2 |
| 5,719,952 A | * | 2/1998 | Rooks ........................... 382/150 |
| 5,771,269 A | * | 6/1998 | Chao ............................... 378/5 |
| 6,069,933 A | * | 5/2000 | Schultz ......................... 378/62 |
| 6,222,902 B1 | * | 4/2001 | Lin et al. ....................... 378/22 |
| 6,324,249 B1 | * | 11/2001 | Fazzio ........................... 378/22 |

* cited by examiner

Primary Examiner—David P. Porta
Assistant Examiner—Allen C Ho
(74) Attorney, Agent, or Firm—Fay, Sharpe, Fagan, Minnich & McKee, LLP

(57) ABSTRACT

The origin of a cone or fan beam of B, γ, or x radiation is moved in a continuous path such as a circle or is stepped among a two-dimensional grid of preselected points. The cone beam of radiation passes through a patient (14) in an imaging region (12) and is detected by a detector array (16). A data collection circuit (20) samples the detector array to generate radiation intensity sub-images. A circuit (56) monitors the shifting of the focal spot and controls an image shifting circuit (58) to shift physical coordinates of the sampled sub-image analogously. A sub-imaging combining circuit (60) interleaves or otherwise combines spatially shifted sub-images. In one embodiment, the combined sub-images forms a higher resolution composite image representation. In another embodiment, a plurality of combined, spatially shifted sub-images are collected at angularly offset orientations around the subject and are reconstructed into a higher resolution composite image representation.

21 Claims, 4 Drawing Sheets

DIGITAL X-RAY IMAGING APPARATUS WITH A MULTIPLE POSITION IRRADIATION SOURCE AND IMPROVED SPATIAL RESOLUTION

BACKGROUND OF THE INVENTION

The present invention relates to the diagnostic imaging arts. It finds particular application in conjunction with digital x-ray imaging and will be described with particular reference thereto. However, it is to be appreciated that the present invention also has application in conjunction with computed tomography (CT) scanning and nuclear cameras and is not limited to the aforementioned application.

The most prominent difference between digital x-ray scanning and classical plane film x-ray is the x-ray detection system. An array of digital detectors replaces the sheet of photosensitive film. Each individual detector within the array detects the intensity of the radiation incident upon its face during the scan and converts that information into an electrical signal. The combined signals are processed and ordered by a computer and converted into a visible display.

Each individual detector reports only one intensity value, the average intensity along a path with about the same cross-section as the individual detector. However, the data is typically treated as if intensity variations are due solely to the x-ray from the source to the center of the detector. In this manner, the detectors can be thought of as individual pixels of a larger image. The smaller the pixels are, the finer the resolution and the more precise the resulting image. Conversely, if the individual detectors are too small, only a small amount of radiation strikes each detector during a sampling interval. Low amounts of received radiation are sensitive to statistical fluctuation and sampling errors.

In a more complex solution, the paths of the central rays are shifted half a pixel and the detectors sampled again. In this manner, the effective number of pixels is doubled. However, mechanically shifting the detector array rapidly and precisely is difficult. Often, vibration occurs providing uncertainty and inaccuracy in the true path of the central rays, which blurs the resultant image.

U.S. Pat. No. 4,637,040 to Sohval and Freundlich alternates between the two x-ray sources. The patent also suggests physically shifting a single x-ray rouse during rotation of a CT scanner, such as with a pair of x-ray tubes or a single tube with two distinct focal spots.

The present invention contemplates a new method and apparatus for increasing the spatial resolution in two dimensions of a digital x-ray system that overcomes the above-referenced problems and others.

SUMMARY OF THE INVENTION

In accordance with one aspect of the present invention, a diagnostic imaging apparatus emits a beam of radiation into an imaging region where it penetrates a subject and is detected on the other side by an array of detectors, and processed into a visual representation of the interior of the subject.

In accordance with another aspect of the present invention, the imaging apparatus emits multiple beams of radiation, each time from a different source point, and combines the detected information into a higher resolution representation of the interior of the subject.

According to a more limited aspect of the present invention, the imaging apparatus uses an x-ray that generates electrons with a cathode and accelerates them towards an anode where they are converted into x-rays, steering the electrons along the way with a plurality of deflectors.

According to a more limited aspect of the present invention, the electrons are moved continuously or incrementally around a closed path on the anode.

According to another aspect of the present invention, a method is provided wherein the resolution of a digital x-ray apparatus is improved by using a plurality of point sources of x-rays, detecting the x-rays after passage through a subject, and combining multiple images into one, higher resolution image.

One advantage of the present invention is that it increases the spatial resolution of a digital x-ray scanning system.

Another advantage of the present invention is that it requires no moving parts to be added to the system.

Another advantage of the present invention is that it increases digital sampling density.

Yet another advantage of the present invention is that it is cost-effective.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

DETAILED DESCRIPTION OF THE PREFERRED EMBODIMENTS

Figure 1:
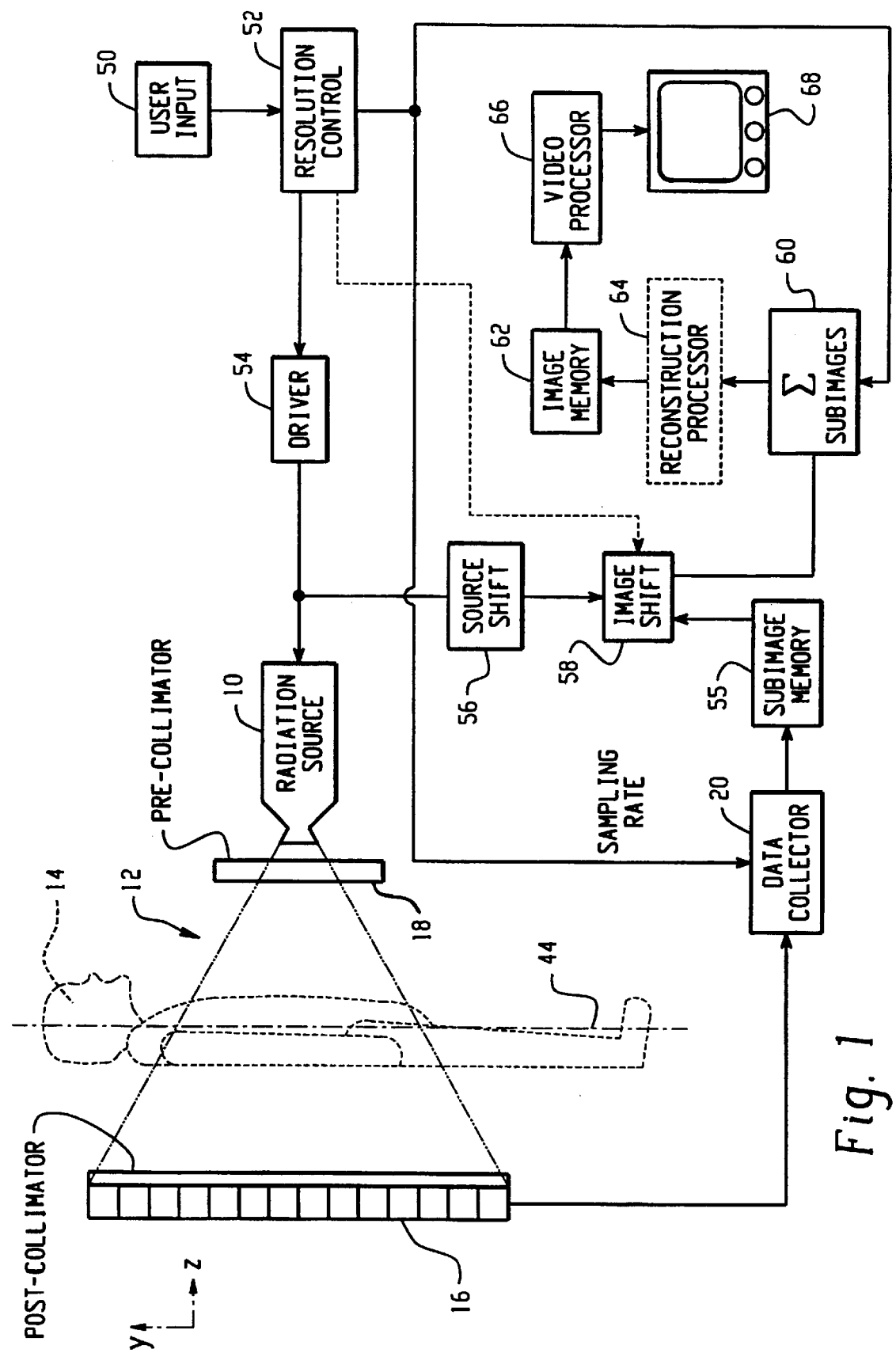
FIG. 1 is a diagrammatic illustration of a digital x-ray scanner in accordance with the present invention.

With reference to FIG. 1, a digital x-ray system is provided. A radiation source 10 emits a cone or fan of B, γ, or other penetrating radiation which passes through an imaging region 12 and through a subject 14 to a two-dimensional radiation detector array 16. In a CT embodiment, a fan or cone of radiation is projected onto a one or two-dimensional array. The x-ray source is mounted for rotation about the subject. The detectors either rotate with the x-ray source or extend in a circumferential arc around the subject. In nuclear medicine, the radiation source is a radioisotope.

The x-ray or other radiation is differentially attenuated by the tissue along each ray between the source and individual detectors. Optionally, a collimator 18 collimates the radiation beam into individual beams focused on the central portion of each detector. Physical filters for beam hardness correction are optionally disposed between the source and the subject 14. Each individual detector in the detector array 16 senses the intensity of the x-rays incident upon its face. This intensity value is turned into a gray scale value which is read by a data collection circuit 20. The gray scale values range from white to black, black corresponding to all of the x-rays reaching the detector, and white corresponding to none of the x-rays reaching the detector. Typically, the detection devices are capable of resolving approximately $2^{32}$ gray scale values, i.e., resolve the gray scale with 32 bit accuracy.

In the simplest case, the radiation source 10 emits x-rays from a stationary point or focal spot, which provides the detector array 16 with only one view of the subject 14. Subsequently, each individual detector reports one intensity value to a data collection circuit 20. The single set of projection data from the data collection circuit 20 is the electronic image representation. In the CT embodiment, each single set of projection data is one of the views for collective reconstruction into an image.

Figure 2:
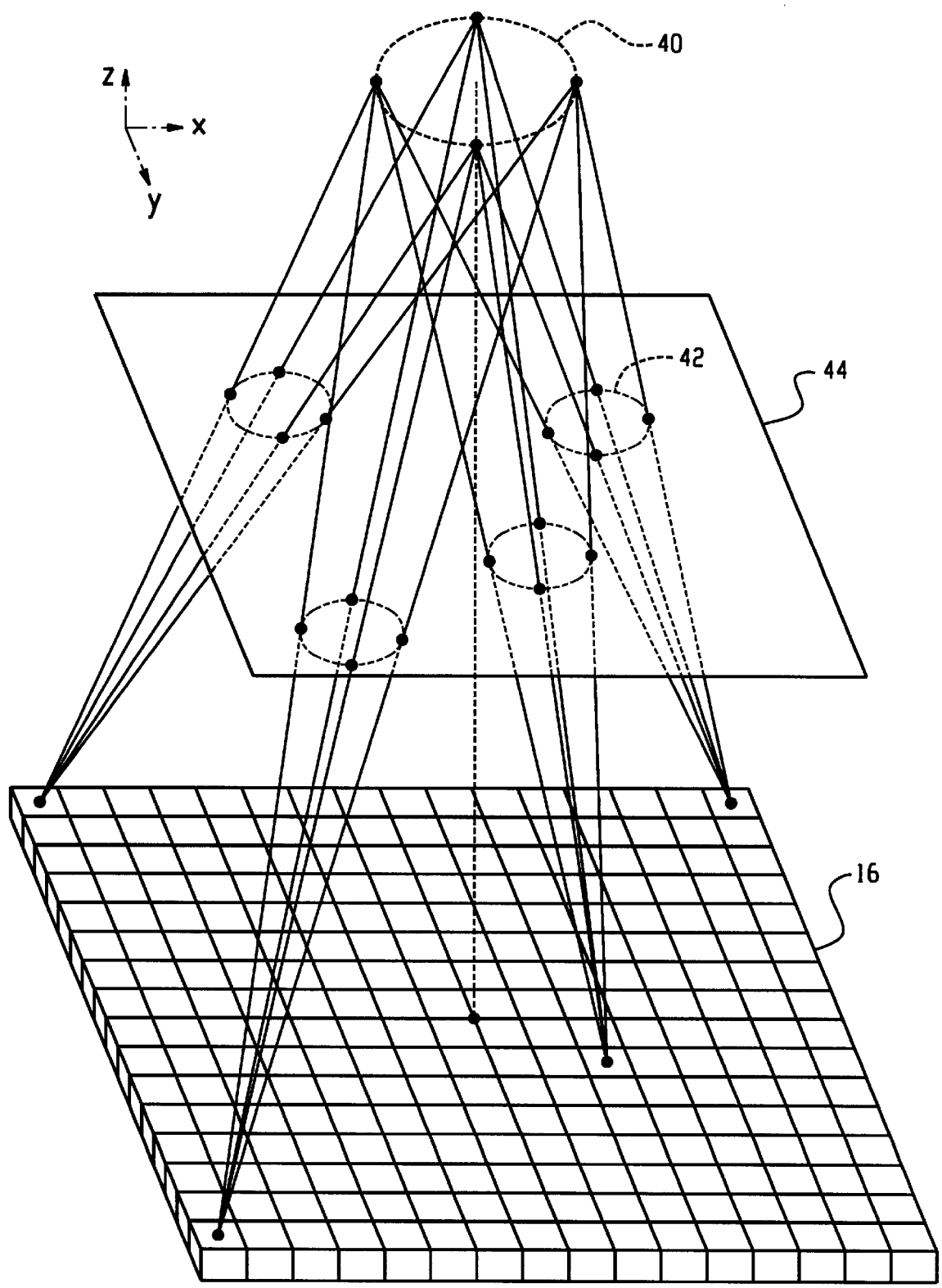
FIG. 2 is an x-ray trajectory plot that illustrates the path of a plurality of x-rays from an oscillating source, through a plane of imaging, to an array of detectors in accordance with the present invention.

In accordance with the present invention, the x-ray source 10 has a mechanism to vary the position of the focal spot or other source of the x-rays in two dimensions, for the purpose of providing the detector array 16 with multiple different views of the subject 14. This concept is illustrated in FIG. 2. With reference to FIG. 2, the source moves about a source path 40, a circle in the illustrated embodiment.

As the source moves along its path, the ray seen by any individual one of the detectors traverses a corresponding path 42 through an imaging plane 44. In the illustrated embodiment, the source is positioned at each of four locations along the source path 40. Of course, the source can be positioned at a larger or smaller number of positions, or can move continuously around the path 40.

With reference again to FIG. 1, a user input device 50 enables the user to instruct the system regarding a desired resolution improvement. A resolution control circuit 52 issues control signals to an x-ray source driver circuit 54 which causes the x-ray source to move continuously or intermittently around the source path 40. The resolution control circuit also sends a sampling signal to the data collection circuit 20 to control sampling of the detector array in coordination with movement of the x-ray source. After the data is collected at one of the positions of the x-ray source, the collected data is moved to a sub-image memory 55. A source shift monitoring circuit 56 monitors movement of the x-ray source and sends a corresponding signal to an image shifting circuit 58. More specifically, as seen in FIG. 2, the data sensed by any given pixel of the array shifts along the path 42 on the image plane. The image shift circuit 58 creates a corresponding shift in the data. An image combining or reconstruction device 60 combines the shifted data. In the digital x-ray embodiment, the combined, shifted data is loaded into an image memory 62. In the CT embodiment, each of the combined, shifted data sets is one view. The one or two-dimensional views generated at different angular orientations around the subject are reconstructed by a reconstruction processor 64 using a convolution-backprojection or other conventional reconstruction algorithm into a two or three-dimensional image representation that is loaded in the image memory 62. In nuclear cameras, volume images are generated analogously from the γ radiation emitted by radioisotopes. A video processor 66 converts images from the image memory into appropriate format for display on a human-readable monitor 68, such as a video monitor, LCD display, active matrix display, or the like.

Figure 3:
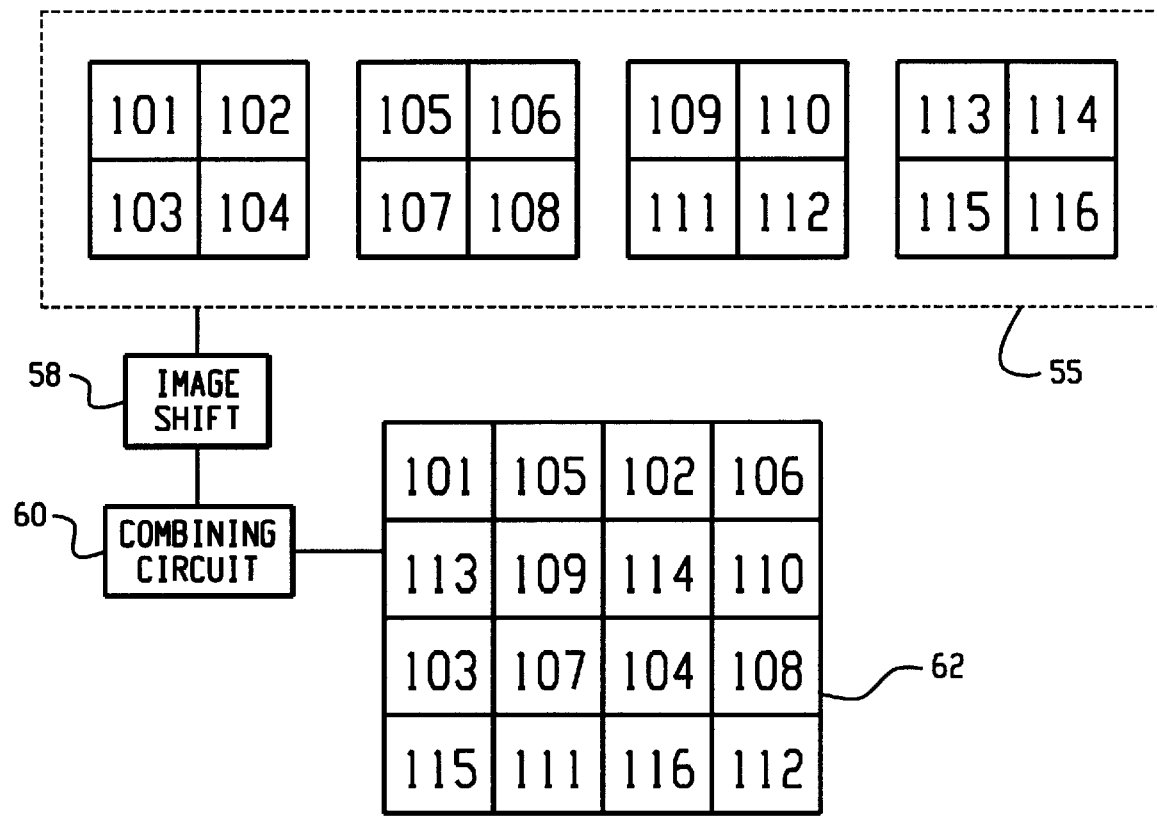
FIG. 3 is a diagrammatic illustration of the reconstruction process in accordance with the present invention; and, FIG. 4 is a cross-sectional view of an x-ray emitter looking in along the z-axis in accordance with the present invention.

A four sampling point embodiment of this concept is illustrated in FIG. 3. Although circular paths are illustrated, it is to be appreciated that other trajectories are also contemplated. In this example, there are four detectors in the array 16 and four sub-images each containing four pixels are generated. Pixel values 101, 105, 109, and 113 are sampled by the upper left detector. Pixel values 104, 108, 112, and 116 are sampled by the lower right detector, and so forth. As the x-ray source rotates clockwise around the path 40, data is collected at four points. The size of the source path 40 is selected relative to the geometry of the image plane and the detector array such that the second sampling position 102, 106, 110, 114 is shifted by a half pixel to the right. In the third position around the source circle, each ray passes through the image plane a half pixel to the right and a half pixel down and is sampled as sample values 104, 108, 112, 116. In the fourth position of the source around the path 40, the ray passes through the image plane a half pixel below the first sampling position. The shifting circuit 58 shifts each of the four sub-images by a half pixel in the appropriate lateral and vertical direction and the combining processor 60 loads the shifted images into the image memory 62. Of course, this four element array is for simplicity of illustration. In practice, arrays are more commonly 256×256, 512×512, 1024×1024, or the like.

Figure 4:
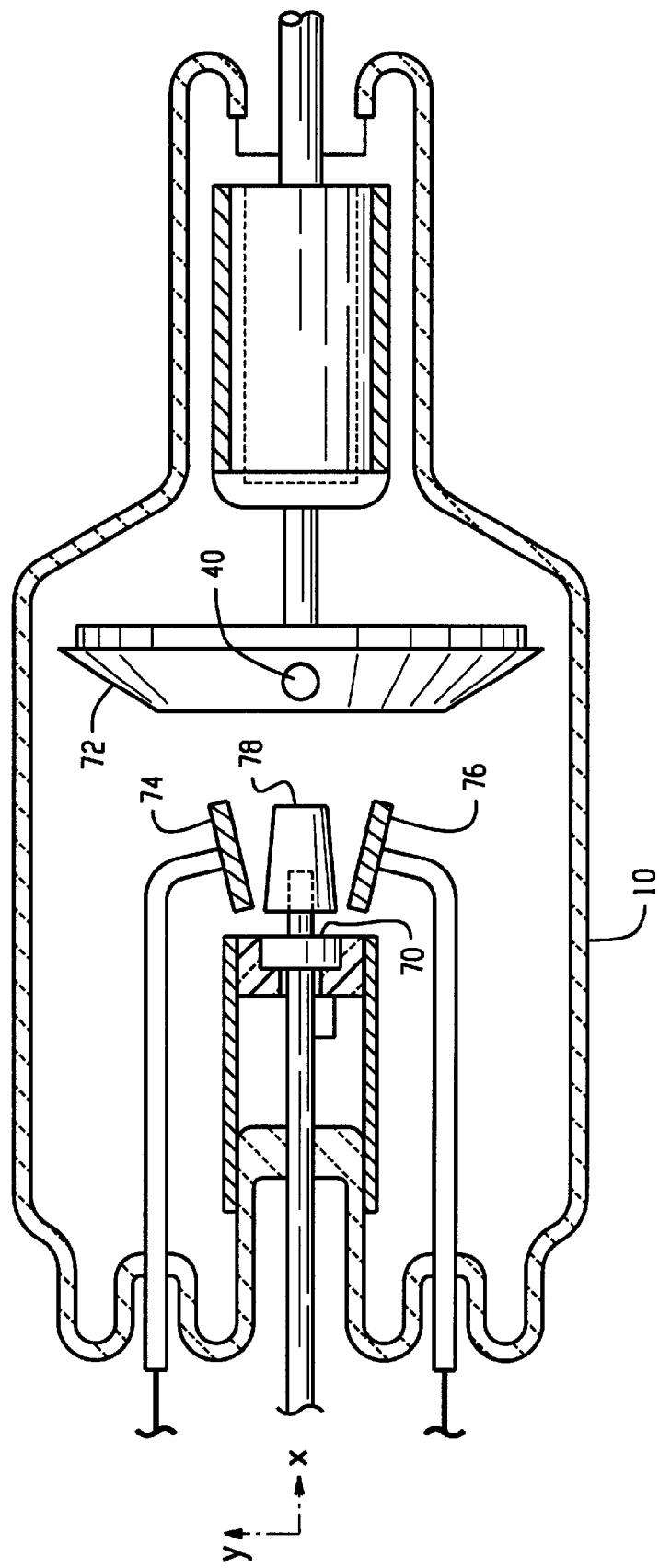

With reference to FIG. 4, the x-ray source is an x-ray tube, in the preferred embodiment. The x-ray tube 10 includes a cathode 70 having a filament and a rotating anode 72. Optionally, the anode can be stationary. Beams of electrons emanating from the filament are accelerated toward the anode and deflected around or to selected points along the source path 40 by the four deflection plates 74, 76, 78, 80,(80 behind 78). Two of the deflection plates 74, 76 control the movement of the beam in the y-direction, and two of the plates 78, 80 control the movement of the beam in the x-direction.

In the preferred embodiment, the voltage applied to the deflection plates varies sinusoidally. Plates 78 and 80 are 90° out of phase with respect to plates 74 and 76. As a result, the electron beam traces a circle that processes about the source path 40 continuously. Alternately, the voltages can be applied to the deflection plates in steps to step the electron beam around the path 40 in steps.

Alternate deflection techniques are also contemplated. For example, magnetic coils can be utilized to deflect the electron beam. As yet another alternative, the x-ray tube can be mechanically moved. As yet another example, the cathode or the anode can be moved within the x-ray tube. As yet another option, the x-ray tube can have multiple cathodes, each focused on an incrementally shifted portion of the anode so that the focal spot is shifted by switching from cathode to cathode. As yet another option, a single cathode can be provided with multiple, offset filaments.

It is to be appreciated that the focal spot can be moved in other than circular trajectories. For example, the detector array can be a one-dimensional array of detectors. The focal spot is then swept back and forth either in steps or continuously in a direction parallel to the one-dimensional array. After sampling the detector array with the x-ray spot in each of a plurality of positions, e.g., four, the subject is indexed relative to the x-ray source and detector array in a direction perpendicular to the detector array. In the new position, the focal spot is again swept and another series of one-dimensional images collected. The sub-images of each line are interleaved and the lines are stacked to form a two-dimensional image. Alternately, the x-ray source and detector can be rotated around the subject and the interleaved data lines reconstructed to form a slice image representation. This same principal can be extended to volumetric images using either two-dimensional arrays or physically stepped one-dimensional arrays.

With two-dimensional detector arrays, various patterns for moving the focal spot are contemplated. For example, the focal spot can be stepped among the four corners of the square. For a finer resolution, the focal spot can be stepped among an nxn array of linear positions arranged in a grid, where m,n are plural integers. As another option, a large number of shifted images are generated and stacked. The pixels of the resultant image are projected through the stacked images and weightedly averaged. This technique is particularly advantageous when the focal spot is not sampled at a periodically changing position and where the resolution of the final image does not match the resolution of the interleaved shifted images.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. An imaging apparatus comprising:
   a radiation source for projecting a beam of radiation through an imaging region;
   a detector array disposed across the imaging region from the radiation source for receiving radiation which has traversed the imaging region and converting received radiation into lower resolution electronic projection images;
   a data collection circuit for collecting the lower resolution projection images from the detector array;
   a driver for moving the radiation source relative to the detector array;
   a data shifting circuit connected with the driver for shifting coordinates of the lower resolution projection images from the data collection circuit in accordance with the relative movement of the radiation source;
   a shifted data combining circuit for combining shifted the lower resolution projection images from the data collection circuit generated at a plurality of shifts of the radiation source to generate a higher resolution projection image that has higher resolution than the lower resolution projection images.

2. The imaging apparatus as set forth in claim 1 wherein the radiation source includes an x-ray tube and the driver circuit moves a focal spot of the x-ray tube.

3. The imaging apparatus as set forth in claim 2 wherein the radiation source includes an x-ray tube having a cathode for generating electrons which are accelerated toward an anode and a plurality of deflectors for deflecting the electron beam such that the radiation beam moves in a pattern on the anode under the control of the driver circuit.

4. The imaging apparatus as set forth in claim 3 wherein the driver moves the focal spot in a continuous pattern.

5. The imaging apparatus as set forth in claim 3 wherein the driver steps the focal spot among a plurality of preselected locations on the anode.

6. An imaging apparatus comprising:
   a means for projecting a beam of radiation through an imaging region;
   a detector array means disposed across the imaging region from the radiation source for receiving radiation which has traversed the imaging region and converting received radiation into lower resolution projection image representations;
   a means for moving the radiation beam relative to the detector array;
   a means for shifting coordinates of the lower resolution projection image representations in accordance with relative movement of the radiation beam;
   a means for summing the lower resolution projection image representation collected at a plurality of angular increments of the radiation beam into a higher resolution projection image representation;
   an image memory means for receiving and storing the image representation.

7. An apparatus for providing a projection image of a subject located in an imaging region with data sampled from the subject using penetrating radiation, the apparatus comprising:
   (a) a source of penetrating radiation that provides a beam of radiation that is transmitted through the subject;
   (b) a stationary array of detectors for detecting the radiation from the source after passage of the radiation through the subject;
   (c) a means for displacing the source of the radiation in two dimensions causing the radiation emitted by the source to traverse a plurality of paths through the subject and to be detected by the detector array to provide the sampling data, portions of the sampling data being offset from at least another portion of the sampling data;
   (d) a means for processing detected radiation by combining the offset portions of sampling data into a single projection image representation having increased sampling density to provide increased spatial resolution in the image representation.

8. The apparatus as set forth in claim 7 wherein the radiation source includes a target anode for emitting radiation in response to a beam of electrons colliding therewith and a means of deflection for deflecting the electron beam in two dimensions between a plurality of focal spots on the anode.

9. The apparatus as set forth in claim 8 wherein the means for deflecting the beam of electrons includes at least three electrostatic or magnetic elements which deflect the beam in two dimensions.

10. The apparatus as set forth in claim 8 wherein the deflecting means causes the focal spot of the beam of electrons on the anode to move sinusoidally in two dimensions.

11. The apparatus as set forth in claim 7 wherein the radiation source emits a cone beam of radiation, and further including post patient collimator means for reducing the height and width of the radiation beam which is detected by the detector means, and means for further increasing the sampling density.

12. The apparatus as set forth in claim 11 wherein the means for further increasing the sampling density includes a plurality of point sources of radiation within the source located on a source circle projected on the anode.

13. An apparatus for providing a projection image of a subject located in an imaging region, the apparatus comprising:
   (a) a source of penetrating radiation which transmits radiation through the subject;
   (b) a detector array which detects the radiation from the source after passage of the radiation through the subject, the detector array including a two-dimensional array of individual square detectors disposed substantially uniformly along a fixed support adjacent the imaging region across from the source of the radiation, the detectors having a common dimension in two orthogonal directions, such that a projection image of corresponding resolution is generated;

(c) a means for displacing the source of the radiation in two dimensions in a plane parallel to the detector array causing the radiation emitted by the source to traverse a plurality of shifted paths through the subject, the paths shifted by a fraction of the common dimension and to be detected by the detector means to provide a plurality of projection images corresponding to the shifted paths;

(d) a means for shifting the projection images by the fraction of the common dimension and summing the shifted projected images to generate a projection image with finer resolution than shifted projection images.

14. A method of improving the spatial resolution of projection images constructed by a digital x-ray scanner, having a source of penetrating radiation for transmission through a subject in an imaging region, a detector array to detect the radiation transmitted through the subject along a plurality of rays, the method comprising:

(a) increasing the sampling density by interleaving radiation rays, including:
    emitting radiation rays from the source, and
    varying a position of the source relative to the detector in two dimensions;

(b) processing the detected radiation at the varied source positions to provide increased spatial resolution of an output projection image.

15. A method of improving the spatial resolution of projection images, the method comprising:

(a) increasing the sampling density by interleaving radiation rays, including:
    emitting radiation from the source along rays, and
    shifting a position of the source in two dimensions;

(b) reading a set of data at each source position, each set of data representing a lower intensity projection image;

(c) spatially shifting the data sets in accordance with corresponding shifted positions of the x-ray source; and (d) combining the spatially shifted data sets to sum the spatially offset lower intensity projection images into a single higher resolution projection image.

16. The method as set forth in claim 15 further including:

repeating steps (i) (ii), and (iii) while moving the radiation source and detector array around the subject;

reconstructing the combined spatially shifted data sets generated as the source and detector array are moved around the subject into the output.

17. A method of diagnostic imaging comprising:

accelerating electrons toward a focal spot on an anode to generate a beam of radiation;

passing the radiation beam through an imaging region;

converting radiation passing through the imaging region into a two-dimensional array of intensity values;

sampling the intensity values;

moving the focal spot around the anode to a plurality of locations;

shifting the sampled two-dimensional arrays of intensity values in accordance with shifting of the focal spot;

interleaving the shifted two-dimensional arrays of intensity values into a projection image representation.

18. The method as set forth in claim 17 wherein the focal spot is moved in a circular path on the anode.

19. The method as set forth in claim 17 wherein the focal spot is stepped among a two-dimensional array of locations on the anode.

20. The method as set forth in claim 17 wherein the focal spot moves continuously on the anode and wherein each sampled array of intensity values is shifted in accordance with a median position of the focal spot during a sampling interval.

21. A method of diagnostic imaging comprising:

projecting radiation from a focal spot through a subject;

detecting the radiation with an array of radiation detector elements to generate a projection image whose resolution corresponds to physical dimensions of the detector elements;

shifting the focal spot such that the generated projection image is shifted by a fraction of the detector element dimensions;

repeating the shifting step with the focal spot shifted to a plurality of positions in two dimensions parallel to the detector array to generate a plurality of projection images all shifted by a fraction of a detector element dimension in different directions in the two dimensions parallel to the detector array;

shifting and summing the plurality of shifted projection images to generate a single projection image whose resolution is finer than the physical dimensions of the detector elements.

* * * * *